(12) United States Patent
Figueredo de Santana et al.

(10) Patent No.: US 11,255,685 B2
(45) Date of Patent: Feb. 22, 2022

(54) REAL-TIME ROUTE DETERMINATION BASED ON LOCALIZED INFORMATION

(71) Applicant: International Business Machines Corporation, Armonk, NY (US)

(72) Inventors: Vagner Figueredo de Santana, São Paulo (BR); Andrea Britto Mattos Lima, São Paulo (BR); Diego Brito Veiga, Campinas (BR); Pablo Gonzalez, São Paulo (BR)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 267 days.

(21) Appl. No.: 16/541,454

(22) Filed: Aug. 15, 2019

(65) Prior Publication Data

US 2021/0048303 A1 Feb. 18, 2021

(51) Int. Cl.
*G01C 21/34* (2006.01)
*G01C 21/36* (2006.01)
(Continued)

(52) U.S. Cl.
CPC ...... *G01C 21/3484* (2013.01); *A61B 5/02055* (2013.01); *A61B 5/165* (2013.01);
(Continued)

(58) Field of Classification Search
CPC ............ G01C 21/3484; G01C 21/3461; G01C 21/3667; A61B 5/165; A61B 5/18;
(Continued)

(56) References Cited

U.S. PATENT DOCUMENTS 6,227,862 B1 5/2001 Harkness
6,599,243 B2 7/2003 Woltermann et al.
(Continued)

FOREIGN PATENT DOCUMENTS

CN 102490701 A 6/2012
CN 107531249 A 1/2018
(Continued)

OTHER PUBLICATIONS

Healey et al., "Detecting Stress During Real-World Driving Tasks Using Physiological Sensors" HP, Dec. 17, 2004 (22 pages).
(Continued)

*Primary Examiner* — Ryan W Sherwin
(74) *Attorney, Agent, or Firm* — Cantor Colburn LLP; Joseph Petrokaitis

(57) ABSTRACT

A real-time route determination system includes one or more communication devices in signal communication with a route server system. Each communication device is configured to receive one or both of vehicle data and user data to determine a stress-level based on one or both of the vehicle data and the user data. The route server system is configured to determine at least one navigation route in real-time based in part on the stress-level, and to output a route signal indicative of the at least one navigation route. The communication device displays a graphical map including a graphical route displaying the at least one navigation route.

8 Claims, 9 Drawing Sheets

(51) Int. Cl.
*A61B 5/16* (2006.01)
*A61B 5/18* (2006.01)
*A61B 5/0205* (2006.01)
*A61B 5/00* (2006.01)
*A61B 5/024* (2006.01)
*A61B 5/01* (2006.01)

(52) U.S. Cl.
CPC ............ *A61B 5/18* (2013.01); *G01C 21/3461* (2013.01); *G01C 21/3667* (2013.01); *A61B 5/0077* (2013.01); *A61B 5/01* (2013.01); *A61B 5/024* (2013.01); *A61B 5/4266* (2013.01); *A61B 5/4803* (2013.01)

(58) Field of Classification Search
CPC ... A61B 5/02055; A61B 5/0077; A61B 5/024; A61B 5/01; A61B 5/4266; A61B 5/4803
See application file for complete search history.

(56) References Cited

U.S. PATENT DOCUMENTS

| | | |
|---|---|---|
| 7,389,178 B2 | 6/2008 | Raz et al. |
| 8,204,786 B2 | 6/2012 | Leboeuf et al. |
| 8,630,768 B2 | 1/2014 | Mcclellan et al. |
| 8,698,639 B2 | 4/2014 | Fung et al. |
| 8,786,421 B2 | 7/2014 | Dozza |
| 2008/0255722 A1 | 10/2008 | Mcclellan et al. |
| 2010/0217099 A1 | 8/2010 | Leboeuf et al. |
| 2012/0290215 A1 | 11/2012 | Adler et al. |
| 2013/0070043 A1 | 3/2013 | Geva et al. |
| 2013/0226408 A1 | 8/2013 | Fung et al. |
| 2017/0105667 A1 | 4/2017 | Wei et al. |
| 2017/0193819 A1 | 7/2017 | Vandikas et al. |
| 2017/0200449 A1 | 7/2017 | Penilla et al. |
| 2018/0288586 A1* | 10/2018 | Tran ........................ A63B 69/36 |
| 2019/0316922 A1* | 10/2019 | Petersen ............ G01C 21/3617 |

FOREIGN PATENT DOCUMENTS

| | | |
|---|---|---|
| EP | 2711226 A1 | 3/2014 |
| WO | 33070093 A1 | 8/2003 |
| WO | 2018009224 A1 | 1/2018 |

OTHER PUBLICATIONS

Wikipedia "Travelling salesman problem" <URL: https://en.wikipedia.org/wiki/Travelling_salesman_problem> [accessed Aug. 6, 2019] (16 pages).

Williams, "Stress from city driving same as skydiving: MIT study" New York Daily News, Jun. 6, 2013 (6 pages).

* cited by examiner

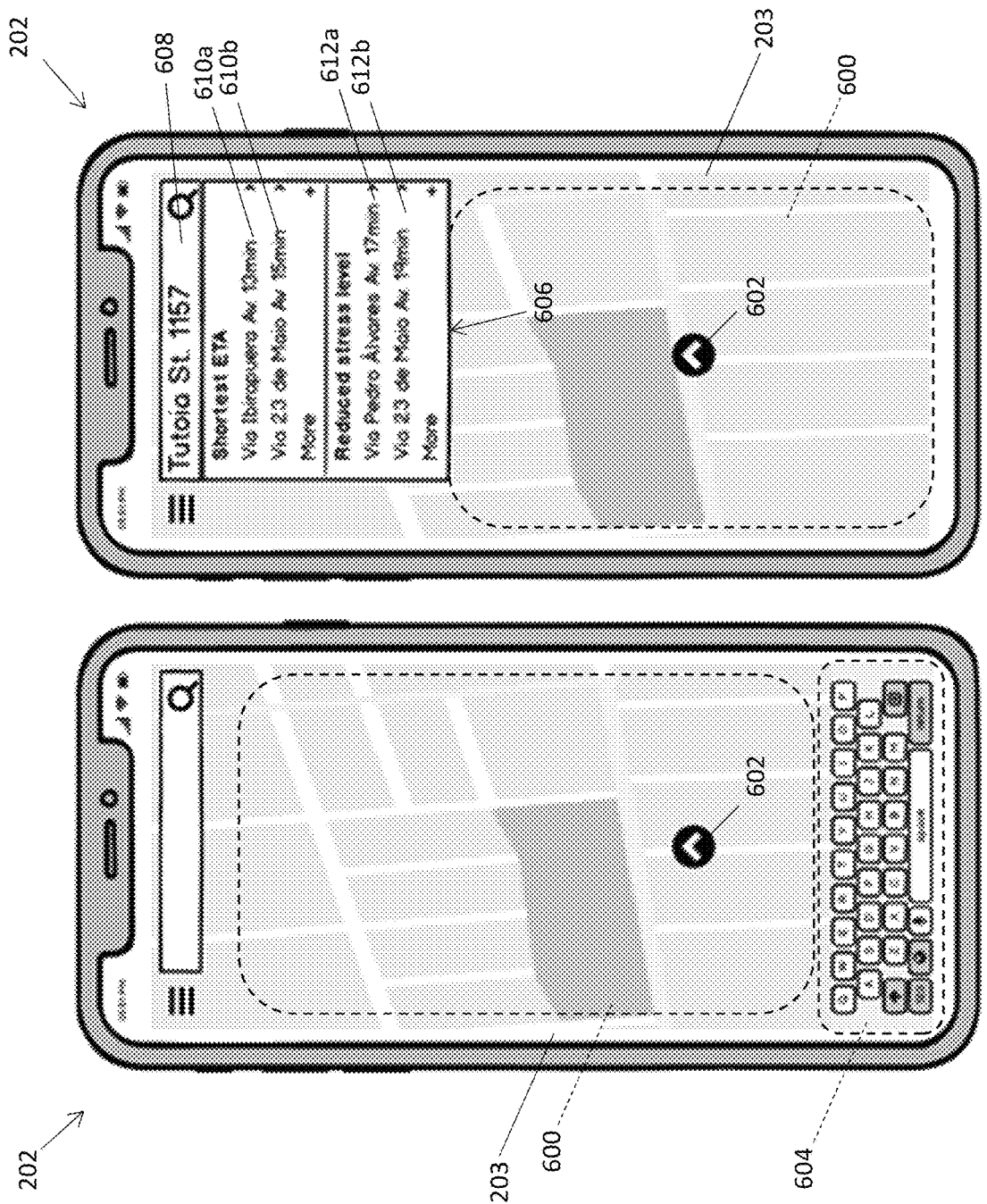

REAL-TIME ROUTE DETERMINATION BASED ON LOCALIZED INFORMATION

BACKGROUND

The present invention relates in general to computing systems, and more specifically, to methods, systems and computer program products that generate navigation data for routing a user to a desired destination.

There is an increasing use of Global Positioning System (GPS)-based navigation systems in vehicles. Such navigation systems receive signals from GPS satellites. Based on received signals, GPS-based navigation systems can identify a vehicle's location in terms of latitude and longitude. The navigation system can also detect the vehicle's speed and direction of travel. With geographic information stored in an on-board computer in the vehicle, the navigation system is capable of providing a user with audio-visually communicated instructions for reaching a desired destination.

SUMMARY

According to a non-limiting embodiment, a real-time route determination system includes one or more communication devices in signal communication with a route server system. Each communication device is configured to receive one or both of vehicle data and user data to determine a stress-level based on one or both of the vehicle data and the user data. The route server system is configured to determine at least one navigation route in real-time based in part on the stress-level, and to output a route signal indicative of the at least one navigation route. The communication device displays a graphical map including a graphical route displaying the at least one navigation route.

According to another non-limiting embodiment, a computer-implemented method is provided to determine a navigation route in real-time. The computer-implemented method comprises receiving, via at least one communication device, one or both of vehicle data and user data; determining a stress-level based on one or both of the vehicle data and the user data. The method further comprises determining, via a route server system in signal communication with the at least one communication device, at least one navigation route in real-time based in part on the stress-level, outputting, via the route server system, a route signal indicative of the at least one navigation route; and displaying, via the at least one communication device, a graphical map including a graphical route displaying the at least one navigation route.

According to yet another non-limiting embodiment, a computer program product comprises a non-transitory storage medium readable by a processing circuit that can store instructions for execution by the processing circuit for performing a method comprising receiving, via at least one communication device, one or both of vehicle data and user data; determining a stress-level based on one or both of the vehicle data and the user data. The method further comprises determining, via a route server system in signal communication with the at least one communication device, at least one navigation route in real-time based in part on the stress-level, outputting, via the route server system, a route signal indicative of the at least one navigation route; and displaying, via the at least one communication device, a graphical map including a graphical route displaying the at least one navigation route.

BRIEF DESCRIPTION OF THE DRAWINGS

The forgoing and other features, and advantages of the disclosure are apparent from the following detailed description taken in conjunction with the accompanying drawings in which:

FIG. 6A depicts operations of a communication device included in a real-time route determination system according to a non-limiting embodiment of the invention;

FIG. 6B depicts operations of a communication device included in a real-time route determination system according to a non-limiting embodiment of the invention;

DETAILED DESCRIPTION

Figure 1:
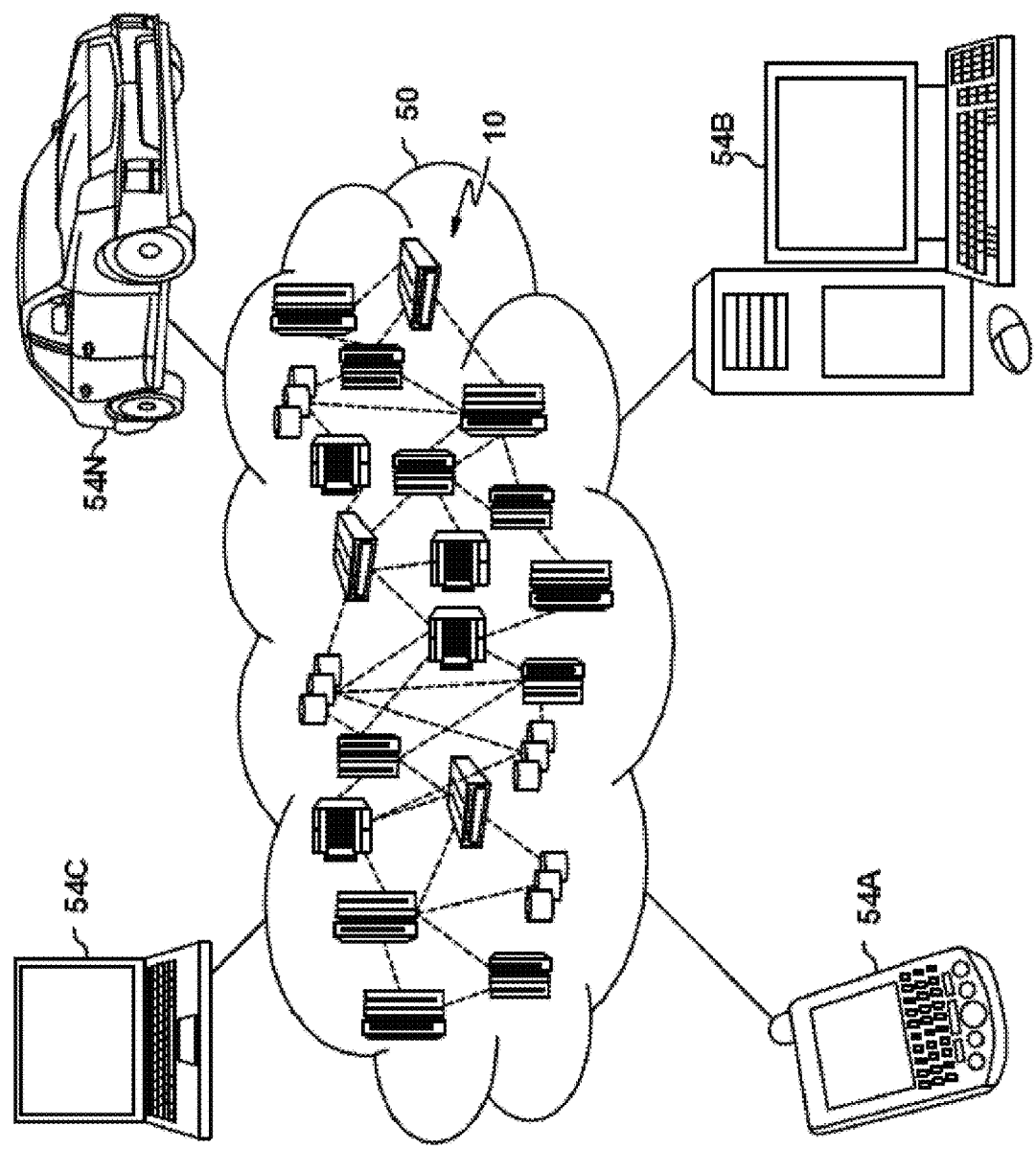
FIG. 1 depicts a cloud computing environment in accordance with a non-limiting embodiment of the invention.

New generation vehicles are currently being employed with state-of-the art communication systems and in-vehicle infotainment systems. These infotainment systems include various sensors capable of obtaining real-time data that can be displayed to a user in real-time, i.e., the actual time during which a process or event occurs. The infotainment system is also configured to connect with various smart automotive technologies like advanced driver assist systems(ADAS), vehicle-to-everything (V2X) connectivity systems, telematics devices, and smart devices such as smartphones, for example, and integrates them with one another other to provide an improved driving experience.

Vehicles and smart devices such as smart phones, for example, to date are known to provide graphical navigation services that present a user with audio graphical navigation directions that define a route from a starting point to a desired destination. These conventional navigation services, however, do not take into account a user's current real-time stress level. As a result, a user who is following a navigation route can experience one or more high-stress events based on the nature of the navigation route before reaching the desired destination.

In one or more non-limiting embodiments of the invention as described herein, a real-time route determination system is provided that determines one or more navigation routes that take into account a user's current stress-level and/or future or predicted stress events the user may encounter while traveling to the destination. The real-time route determination system described herein is configured to analyze a user's localized information such as, for example, health data, physiological data, and current GPS location data to detect increases in stress level then presents the user with a route or a modified route designed to reduce the user's stress-level or route the user around one or more predicted stress events.

It is understood in advance that although this disclosure includes a detailed description on cloud computing, implementation of the teachings recited herein are not limited to a cloud-computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model can include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It can be managed by the organization or a third party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud-computing environment is service oriented with a focus on statelessness, low coupling, modularity, and semantic interoperability. At the heart of cloud computing is an infrastructure comprising a network of interconnected nodes.

Referring to FIG. 1, illustrative cloud computing environment 50 is depicted. As shown, cloud-computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N can communicate. Nodes 10 can communicate with one another. They can be grouped (not shown) physically or virtually, in one or more networks, such as Private, Community, Public, or Hybrid clouds as described hereinabove, or a combination thereof. This allows cloud-computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
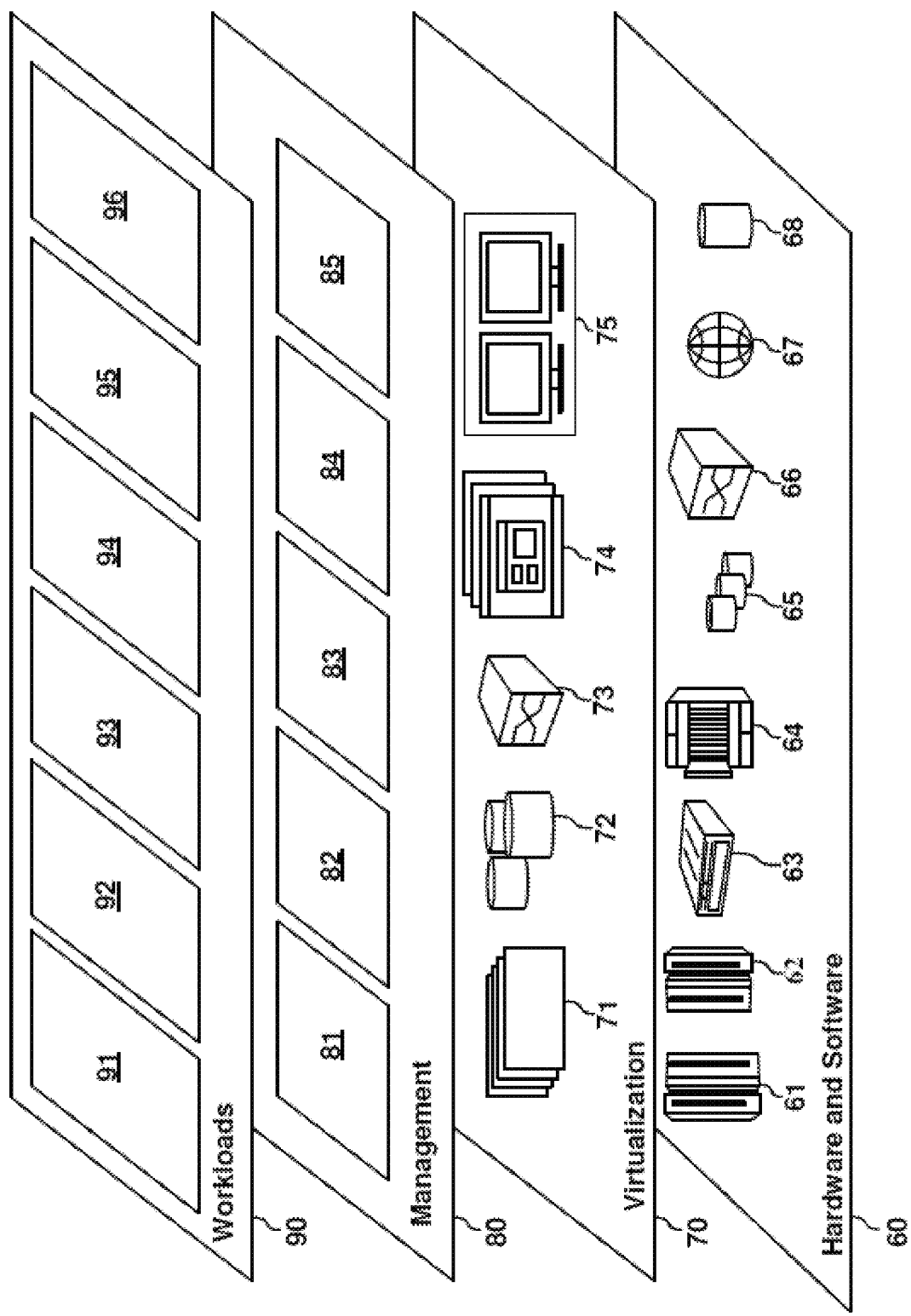
FIG. 2 depicts abstraction model layers in accordance with a non-limiting embodiment of the invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities can be provided: virtual servers 71; virtual storage 72; virtual networks 73, including virtual private networks; virtual applications and operating systems 74; and virtual clients 75.

In one example, management layer 80 can provide the functions described below. Resource provisioning 81 provides dynamic procurement of computing resources and other resources that are utilized to perform tasks within the cloud-computing environment. Metering and Pricing 82 provide cost tracking as resources are utilized within the cloud-computing environment, and billing or invoicing for consumption of these resources. In one example, these resources can comprise application software licenses. Security provides identity verification for cloud consumers and tasks, as well as protection for data and other resources. User portal 83 provides access to the cloud-computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud-computing environment can be utilized. Examples of workloads and functions that can be provided from this layer include: mapping and navigation 91; software development and lifecycle management 92; virtual classroom education delivery 93; data analytics processing 94; transaction processing 95; and ridesharing management for autonomous vehicles 96.

Figure 3:
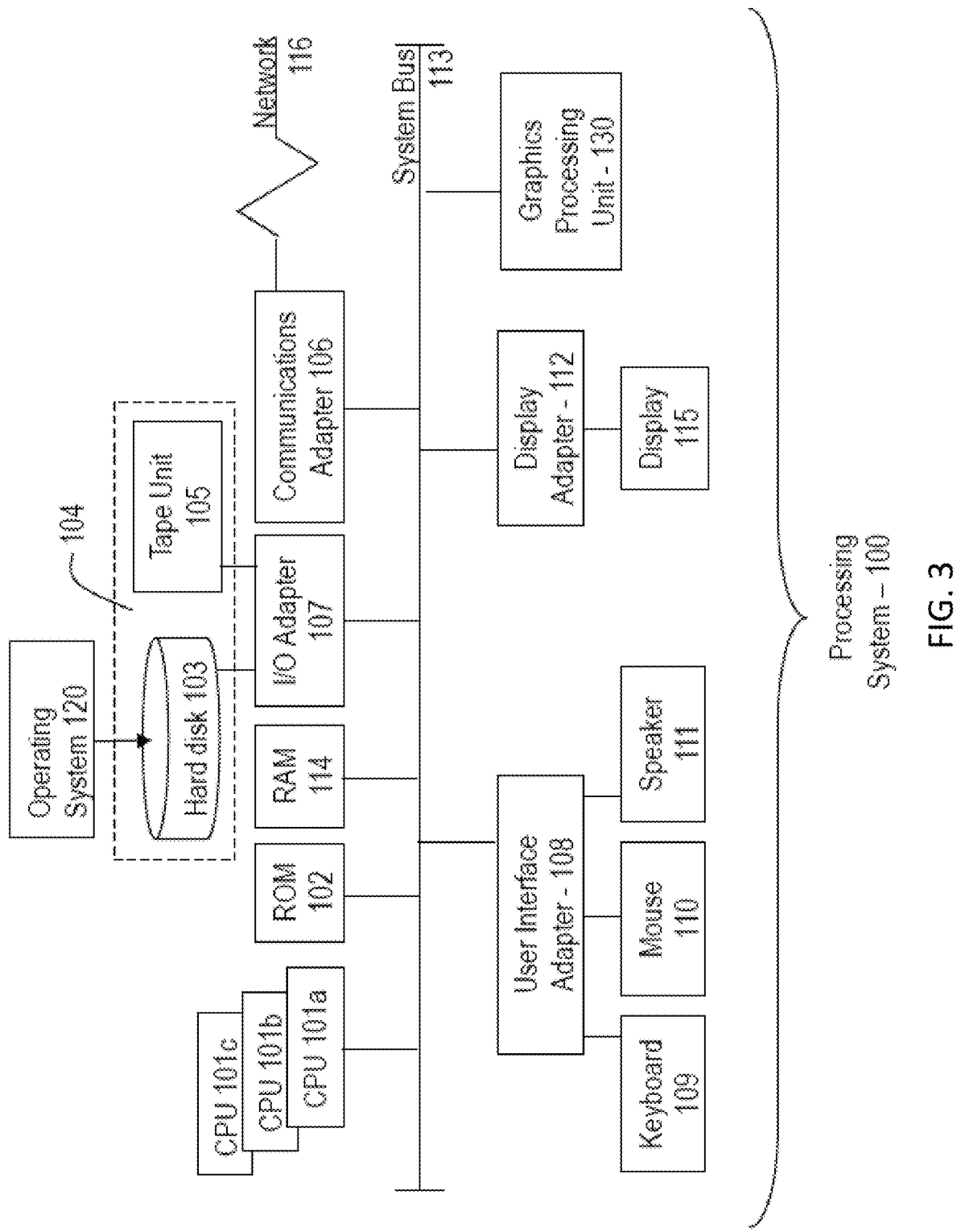
FIG. 3 is a block diagram illustrating one example of a processing system for practice of the teachings herein.

With reference now to FIG. 3, a computer processing system 100 is illustrated according to a non-limiting embodiment of the invention. The processing system 100 includes processing capability in the form of processors 101, storage capability including system memory 114 and mass storage 104, input means such as keyboard 109 and mouse 110, and output capability including speaker 111 and display 115. In one embodiment, a portion of system memory 114 and mass storage 104 collectively store an operating system such as the AIX® operating system from IBM Corporation to coordinate the functions of the various components shown in FIG. 3.

FIG. 3 further depicts an input/output (I/O) adapter 107 and a communications adapter 106 coupled to the system bus 113. I/O adapter 107 can be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Operating system 120 for execution on the processing system 100 can be stored in mass storage 104. A communications adapter 106 interconnects bus 113 with an outside network 116 enabling data processing system 100 to communicate with other such systems. A screen (e.g., a display monitor) 115 is connected to system bus 113 by display adapter 112, which can include a graphics adapter to improve the performance of graphics intensive applications and a video controller. In one embodiment, adapters 107, 106, and 112 can be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnect to bus 113 via user interface adapter 108, which can include, for example, a Super I/O chip integrating multiple device adapters into a single integrated circuit.

In exemplary embodiments, the processing system 100 includes a graphics-processing unit 130. Graphics processing unit 130 is a specialized electronic circuit designed to manipulate and alter memory to accelerate the creation of images in a frame buffer intended for output to a display. In general, graphics-processing unit 130 is very efficient at manipulating computer graphics and image processing, and has a highly parallel structure that makes it more effective than general-purpose CPUs for algorithms where processing of large blocks of data is done in parallel.

Figure 4:
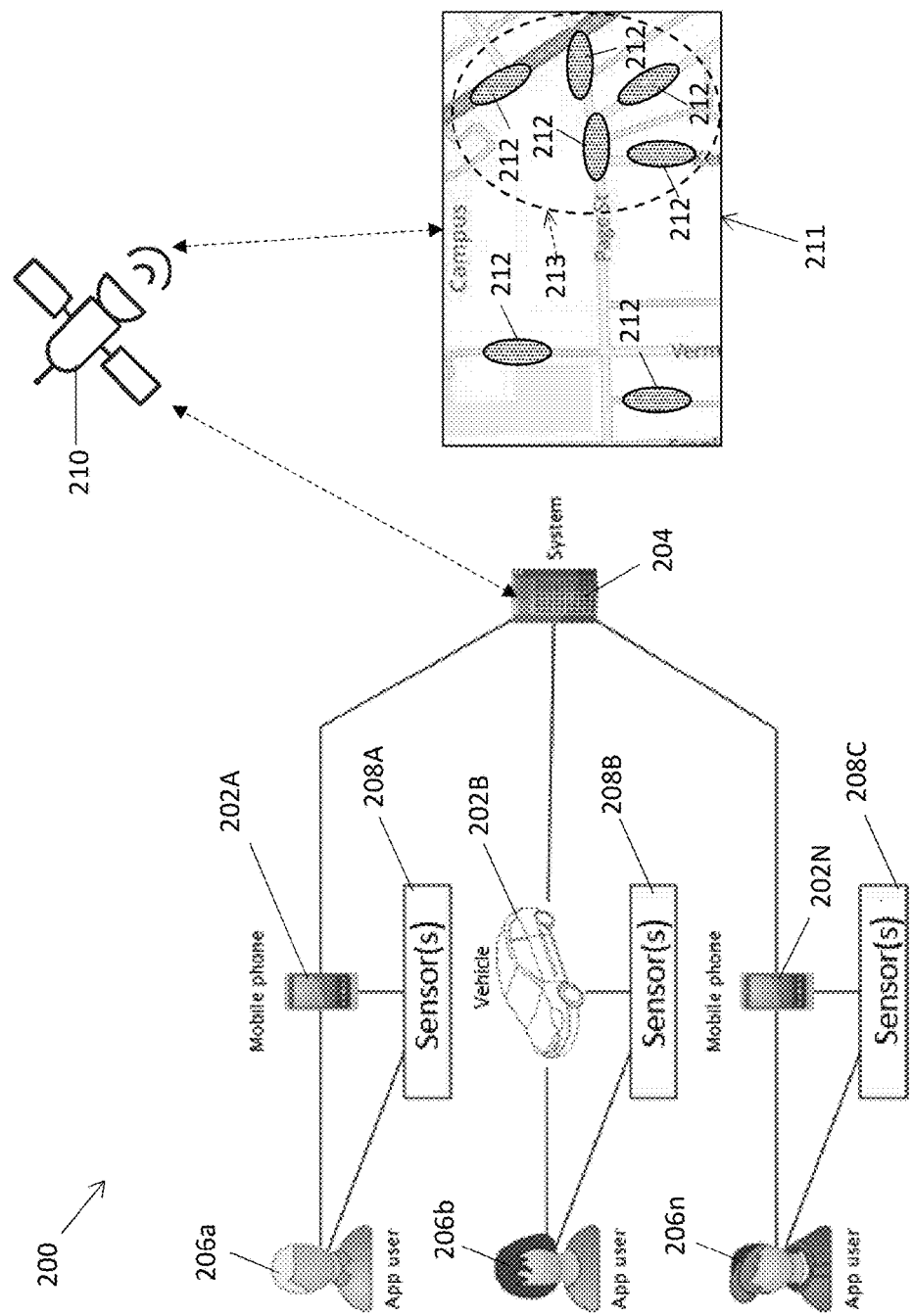
FIG. 4 depicts a real-time route determination system according to a non-limiting embodiment of the invention.

Turning now to FIG. 4, a real-time route determination system 200 is illustrated according to a non-limiting embodiment of the invention. The real-time route determination system 200 includes one or more communication devices 202A, 202B, 202N in signal communication with a route server system 204. The communication devices 202A, 202B, 202N can be operated by a respective user 206A, 206B 206N. Various devices and systems can be employed to establish a communication device 202A, 202B, 202N including, but not limited to, a mobile terminal device such as a laptop computer, a tablet computer, smart devices such as a smart phone, smart watch or other smart wearable device. A vehicle including a communication system capable of processing and exchanging data can also establish a communication device 202A, 202B, 202N as described herein.

Each communication device 202A, 202B, 202N is in signal communication with one or more respective sensors 208A, 208B, 208N. The sensors 208A, 208B, 208N are configured to obtain one or both of vehicle data and user data. The vehicle data includes, but is not limited to, real-time location of a given vehicle, real-time location data of vehicles near a given vehicle, real-time speed data of a given vehicle, braking data of a given vehicle, and real-time lane data of a given vehicle. The term "real-time" as recited herein refers to the actual time during which a process or event occurs. The user data includes localized user data including, but not limited to, health data, physiological data (e.g., heart rate, sweat, tension, body temperature, etc.), and physical user-status data (e.g., facial expressions, voice levels, body movements, etc.). The data provided by the sensors 208A, 208B, 208N can also include external data including weather data, traffic congestion data, road construction data, and lane/street closure data. The types of sensors 208A, 208B, 208N that can be employed to obtain the user data, vehicle data and external data described above include, but are not limited to, heart rate sensors to determine user's heart rate, galvanic skin response sensors configured to monitor skin conductance and the presence of sweat, and cameras to capture a user's fascial expressions. GPS data can also be utilized to calculate a real-time information of the user 206A, 206B, 206N and/or communication device 202A, 202B, 202N such as, for example, real-time location, real-time travel direction, and real-time speed. In cases where the communication device includes a vehicle installed with an infotainment system, the heart rate and galvanic skin sensors can be included in the steering wheel, while the camera and display are included in the infotainment head-up display (HUD).

Figure 5:
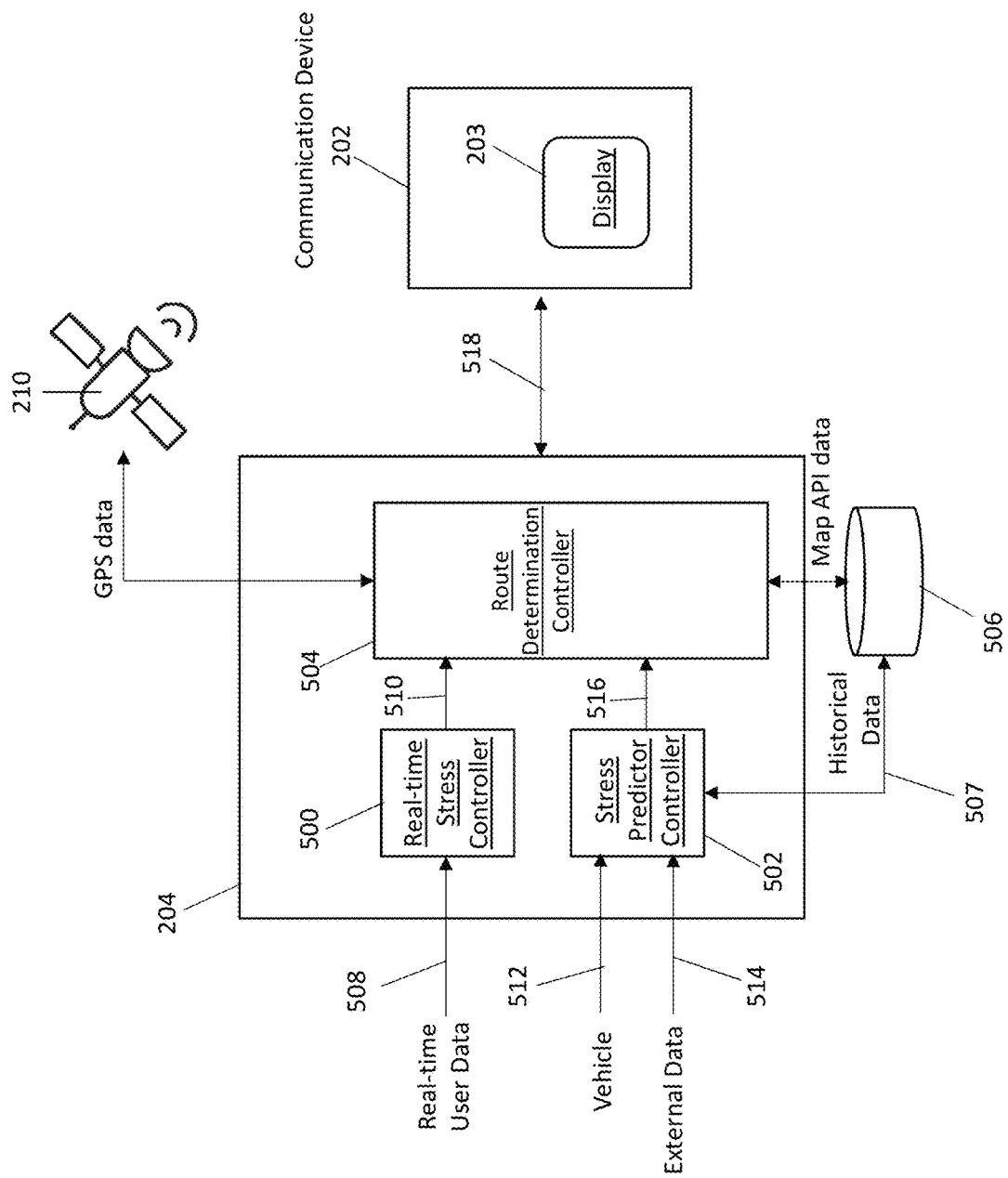
FIG. 5 is a block diagram illustrating a real-time route determination system according to a non-limiting embodiment of the invention.

FIG. 5 depicts a route server system 204, which is non-limiting example of how the route server system 204 (shown in FIG. 4) can be implemented. The route server system 204 includes a computer processing system configured to determine one or more navigation routes in real-time based at least in part on one or both of the vehicle data and the user data. In one or more embodiments of the invention, the route server system 204 is in signal communication with a GPS system 210 to obtain real-time traffic data, along with the communication devices 208A, 208B, 208N (shown in FIG. 4) to obtain the vehicle data and the user data. The GPS system 210 can obtain traffic data by monitoring communication devices configured to share their real-time GPS location data and/or from users that input specific traffic data.

In general, the route server system 204 can include various machine learning algorithms configured to include functionality that is necessary to interpret and utilize the input data from various sources shown in FIG. 5 at 508, 512, 514, 507, 518 (including GPS data). The machine learning algorithms apply machine learning techniques to received training data in order to, over time, create/train/update various models, including, for example, models of person/users 206a, 206b, 206n (shown in FIG. 4). In accordance with aspects of the invention, the models created/trained/updated by the machine learning algorithms can include, but are not limited to, a user stress predictor model (e.g., generated by controller 502), a user real-time stress model (e.g., generated by controller 500), and a user route determination model (e.g., generate by the controller 504). The machine learning algorithms generate the above-described models by extracting features from training data in order to "classify" the training data against the models and uncover relationships between and among the classified training data. Examples of suitable implementations of the machine learning algorithms include but are not limited to neural networks, support vector machines (SVMs), logistic regression, decision trees, hidden Markov Models (HMMs), etc. The learning or training performed by the machine learning algorithms can be supervised, unsupervised, or a hybrid that includes aspects of supervised and unsupervised learning. Supervised learning is when training data is already available and classified/labeled. Unsupervised learning is when training data is not classified/labeled so must be developed through iterations of the machine learning algorithms Unsupervised learning can utilize additional learning/training methods including, for example, clustering, anomaly detection, neural networks, deep learning, and the like. In some embodiments of the invention, training data from a variety of sources can be accumulated and stored (e.g., at the clouding computing system 50 shown in FIG. 1) and provided through a wired or a wireless connection as training data for creating the above-described models.

When the above-described models are sufficiently trained by the machine learning algorithms, the route server system 204 applies "real world" data (e.g., the input data from various sources shown in FIG. 5 at 508, 512, 514, 507, 518 (including GPS data)) to the models in order to generate outputs from the controllers 500, 502, 504. In accordance with aspects of the invention, the outputs from the controllers 500, 502, 504 can be fed back to the route server system 204 and used by the machine learning algorithms as additional training data for creating the above-described models.

In aspects of the invention, the machine learning algorithms are configured to apply confidence levels (CLs) to various ones of their results/determinations in order to improve the overall accuracy of the particular result/determination. When the machine learning algorithms make a determination or generate a result for which the value of CL is below a predetermined threshold (TH) (i.e., CL<TH), the result/determination can be classified as having sufficiently low "confidence" to justify a conclusion that the determination/result is not valid, and this conclusion can be used to determine when, how, and/or if the determinations/results are handled in downstream processing. If CL>TH, the determination/result can be considered valid, and this conclusion can be used to determine when, how, and/or if the determinations/results are handled in downstream processing. Many different predetermined TH levels can be provided. The determinations/results with CL>TH can be ranked from the highest CL>TH to the lowest CL>TH in order to prioritize when, how, and/or if the determinations/results are handled in downstream processing.

In one or more embodiments, the route server system 204 can perform learning based on a particular user. For example, in a given family, different users can drive the family car, and profiles for each user can be saved in a database. The route server system 204 can identify whether the user is Driver A, Driver B, or Driver C (e.g., by user input), and actively build the given user's profile for each under the determination that what is stressful for Driver A may or may not be stressful for Driver B. In addition, the route server system 204 can automatically segment the database and machine learning operations for the different drivers by requiring the driver/user to identify themselves (e.g., using fingerprint recognition) in order to activate the route server system 204.

Referring now to FIGS. 4 and 5, in one or more embodiments of the invention, the route server system 204 can identify a real-time location of a given vehicle, geographical regions 211, nearby vehicles 212 that cause the rise of a user's real-time stress and/or congested traffic areas 213, and can actively determine navigation routes for removing the user 206A, 206B, 206N from the region or location causing the increased stress level. In addition, in accordance with one or more embodiments of the invention, the route server system 204 can utilize historical data indicating historical rises in a user's stress level, predict a future rise in a user's stress level, and proactively determine navigations route(s) that direct the user 206A, 206B, 206N away from those regions or locations that historically induced increased stress levels Returning to FIG. 5, the route server system 204 can be configured to include a real-time stress controller 500, a stress predictor controller 502, and a route determination controller 504. Each of the controller 500, stress predictor controller 502, and route determination controller 504 can include memory and a processor configured to execute algorithms and computer-readable program instructions stored in the memory. In addition, the controller 500, stress predictor controller 502, and route determination controller 504 can all be embedded or integrated in a single controller.

The route server system 204 is also in signal communication with a memory unit or a database 506 that stores a map application programming interface (API) which can be executed by a processor. The database 506 can also store navigation data and historical data. The navigation data includes, for example, real-time global position satellite (GPS) data of one or more vehicles provided by the GPS system 210. The GPS data can also facilitate real-time traffic condition data such as traffic congestion, construction zones, traffic accident information, lane/street closures, etc. In accordance with aspects of the invention, the historical data can include previously detected stress level events indexed to historical events such as previous traffic congestion levels, weather events, etc.

The real-time stress controller 500 is in signal communication with one or more sensors 208A, 208B, 208C (shown in FIG. 4) and is configured to determine a real-time stress level of the user based at least in part on the real-time user data 508. As mentioned herein, the user data includes, but is not limited to, health data, physiological data, and physical user-status data. The health data and/or physiological data includes but is not limited to, heart rate, sweat, tension, body temperature, blood pressure, pulse rate, or other vitals sign data. The physical user-status data includes, but is not limited to, facial expressions, voice levels, body movements, etc.

In one or more embodiments of the invention, the real-time stress controller 500 determines the real-time stress level in response to detecting a change in a user's vitals and/or by comparing the user data to one or more threshold values. For example, the real-time stress controller 500 can compare a user's real-time heart rate to a beats per minute (BPM) threshold. When the user's heat rate exceeds the BPM threshold, the real-time stress controller 500 can detect a high-stress level event where the user is experiencing a high-level of stress or is currently exposed to a high-stress level situation. For example, a user with a heart rate exceeding 100 beats per minute (BPM), for example, or a sudden increase in heart rate (e.g., 60 BPM to 80 BPM within 10 minutes) can be determined to be experiencing high-stress levels or a high-stress level situation. Similarly, the real-time stress controller 500 can also determine an increase in real-time stress levels in response to detecting an increase in body temperature and/or sweat levels. Accordingly, the real-time stress controller 500 can generate a stress detection signal indicating detection of a real-time stress event realized by the user.

The stress predictor controller 502 is in signal communication with one or more sensors 208 (not shown in FIG. 5) along with the database 506, and is configured to predict a future stress level of a user based at least in part on one or both of the vehicle data 512, the external data 514 and/or the historical data 507. As mentioned above, the vehicle data 512 includes, but is not limited to, current vehicle location, location data of vehicles near a given vehicle, speed data of a given vehicle, braking data of a given vehicle, and lane data of a given vehicle. The external data 514 includes, but is not limited to, weather data, traffic congestion data, road construction data, and lane/street closure data.

In one or more embodiments of the invention, the stress predictor controller 502 can employ various machine learning algorithms and/or artificial intelligence logic that analyzes real-time vehicle data 512 and/or the external data 514 along with the historical data 507 to predict a user's future stress levels. For instance, the database 506 can store a history of previous traffic congestion levels indexed to previous high-level stress events. In this manner, when real-time traffic congestion levels match a historical traffic congestion level stored in the database 506, the stress predictor controller 502 can predict that the user will realize an increase in stress and generates a future stress indication signal 516 indicating detection of a future stress event.

In another example, the database 506 can store a history of a user's preferred navigation routes and common driving events. A preferred navigation route can include, for example, a user's route home. A common driving event can include, for example, a user's typical commute from an office complex at end of a workday (e.g., 5 PM). Accordingly, the database 506 can store historical data indicating that the user has previously realized high-levels of stress driving one or more particular routes at approximately 5 PM. In this manner, when a user indicates a destination of "home" at approximately 5 PM during a work week, the stress predictor controller 502 can generate a future stress indication signal 516 indicating detection of a future stress event.

Another example may utilize real-time weather data to predict stress levels of a user. For instance, historical data stored in the database 506 can indicate a user realized increased stress-levels as the user drove through a rainstorm. The stress predictor controller 502 can also be programmed to presume a user's stress-level will increase when encountering various weather conditions such as known raid conditions, ice conditions, icy roads, etc. Accordingly, the external data indicates the presence of nearby high-stress inducing weather conditions, the stress predictor controller 502 can generate a future stress indication signal 516 indicating detection of a future stress event.

The route determination controller 504 is in signal communication with the real-time stress controller 500 and the stress predictor controller 502. The route determination controller 504 is configured to determine one or more navigation routes based on one or both of the real-time stress level indicated by the stress detection signal 510 and/or the future stress level indicated by the future stress indication signal 516. Based on the determined navigate route(s), the route determination controller 504 outputs a route signal 518 indicative of a navigation route to a given communication device 202. Accordingly, the communication device 202 can render a graphical map on a display unit 202, such that the graphical map displays the navigation route that directs the user away from the real-time stress event and/or the predicted stress event.

Figure 6D:
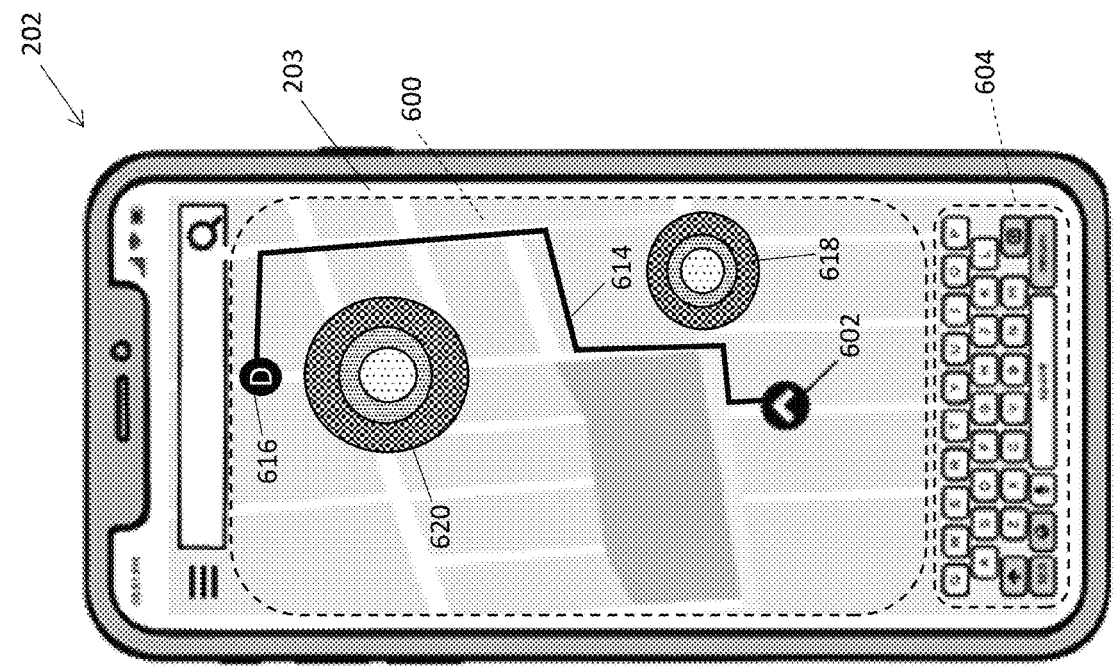
FIG. 6D depicts operations of a communication device included in a real-time route determination system according to a non-limiting embodiment of the invention.
Figure 6C:
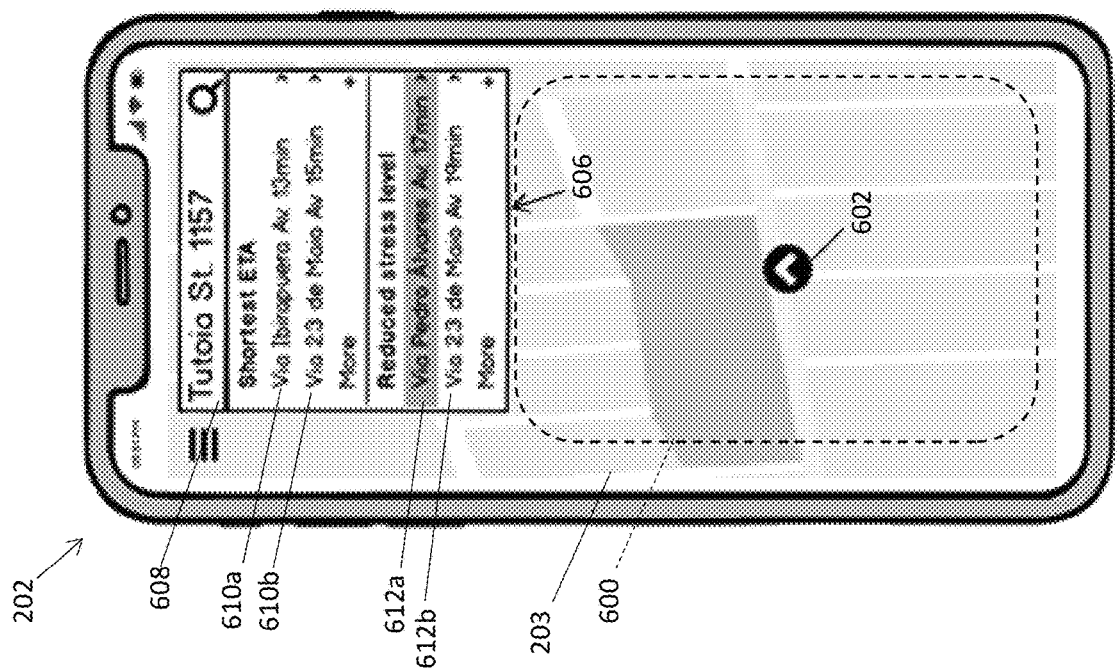
FIG. 6C depicts operations of a communication device included in a real-time route determination system according to a non-limiting embodiment of the invention.

Turning to FIGS. 6A-6C, operation of a communication device 202 included in a real-time route determination system is illustrated according to a non-limiting embodiment. Although in this example the communication device 202 is described as a mobile smartphone, the operation of the communication device is not limited thereto. For example, the operation described with respect to FIGS. 6A-6C can be performed by a navigation and infotainment system installed in a vehicle.

Turning to FIG. 6A, the communication device 202 is shown including a display unit 203 that displays a graphical map 600. The graphical map 600 can be invoked, for example, in response to a user launching a navigation map software application (referred to as an "app"). The graphical map 600 displays a location indicator 602 indicating a current real-time location of the communication device 202 and thus the user's current real-time location. The communication device 202 can further include one or more input units 604 capable of inputting a user input. In this example, the input unit 604 includes a displayable touchscreen keyboard, which allows a user to input a destination.

Referring to FIG. 6B, the communication device 202 is illustrated displaying a route option graphic 606 in response to receiving destination data (e.g., a destination address) 608 input by a user. Based on the input destination data 608, the communication device 202 can determine one or more stress areas and can generate the route option graphic 606 that presents the user with different navigation routes 610a, 610b, 612a, 612b that can be selected by the user. In this example, the selectable navigate routes include different shortest estimated time of arrival (ETA) routes 610a, 610b and a reduced-stress route 612a, 612b. The shortest ETA routes 610a, 610b are aimed at providing the user with a quickest route to the input destination. The reduced-stress routes 612a, 612b are aimed at providing the user with a route to the input destination that avoids areas or driving scenarios that will increase the stress-level of the user, or that will lead the user away from an on-going high-stress scenario. In this example, a user selects one of the reduced-stress routes 612a (see FIG. 6C).

Referring to 6D, the communication device 202 renders a reduced-stress graphical navigation route 614 that will lead the user from their current location 602 to their desired destination 616 corresponding to the input destination address with the aim of avoiding stress-inducing locations or events 618 and 620. In one or more embodiments, the communication device 202 can also render one or more graphical stress indicators 618 and 620 that are displayed on the display unit 203. The graphical stress indicators 618 and 620 indicate a location of a particular stress event occurring in real-time. For example, the communication device 202 can display a first stress indicator 618 that indicates an inclement weather event (e.g., icy roads) and a second stress indicator 620 that indicates a high-congestion traffic area. Accordingly, the display unit 203 can display how the reduced-stress graphical navigation route 614 will lead the user to the intended destination 616 while avoiding stress-inducing areas or events 618 and 620.

Figure 7:
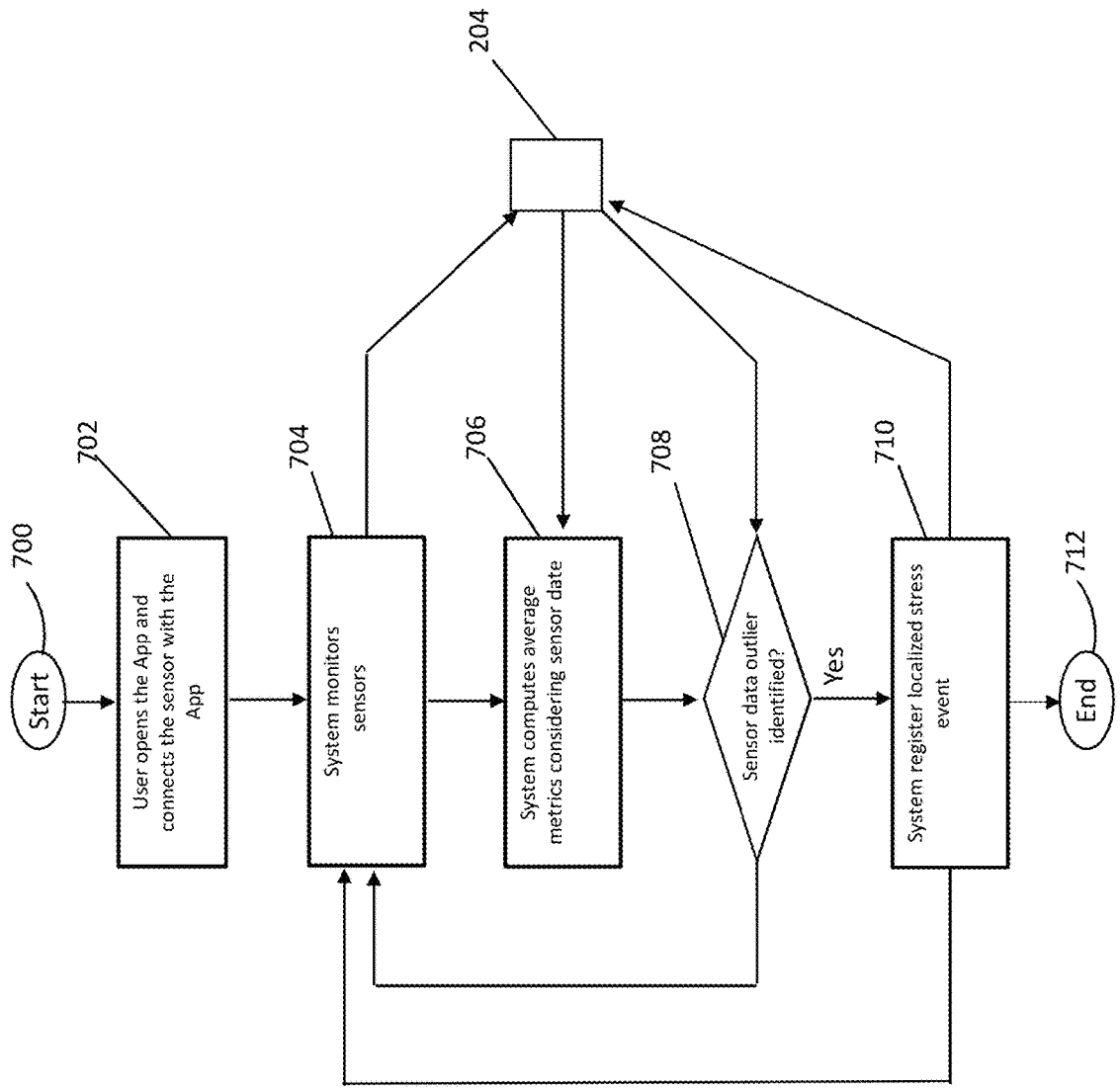
FIG. 7 depicts a flow diagram illustrating a method of determining a stress level of a user according to a non-limiting embodiment of the invention.

With reference now to FIG. 7, a method of determining a stress level of a user is illustrated according to a non-limiting embodiment. The method begins at operation 700, and at operation 702 a user operating a communication device launches a navigation app. In response to launching the navigation app, a graphical map is displayed and data is provided to the communication device. The data is provided by one or more sensors and can include real-time user data, vehicle data, external data, and/or historical data. At operation. At operation 704, the route server system 204 monitors the real-time user data, vehicle data and/or external data. For example, the route server system 204 can monitor real-time data output from various health sensors and physiological sensors such as heart monitor sensors, galvanic skin and/or cameras. At operation 706, the route server system 204 determines average metrics of the monitored health and physiological data. For example, the route server system 204 can monitor a hear rate sensor to determine a user's real-time heart rate (e.g., BPM).

At operation 708, the route server system 204 determines whether an outlier is detected based on the determined health and physiological data. For example, the route server system 204 can compare the real-time heart rate to a BPM threshold. When the real-time heart rate exceeds the BPM threshold, the route server system 204 can detect a physiological outlier. When an outlier is not detected, the method returns to operation 704 and continues monitoring the real-time user data, vehicle data and/or external data provided by the sensors. When, however, an outliner is detected, the method registers the on-going event as a detected stress event at operation 710. In one or more embodiments, the route server system 204 can generate stress detection signal indicative of the detected stress event, store the detected stress event and its associated physiological data in a database as historical data, and the method ends at operation 712.

Figure 8:
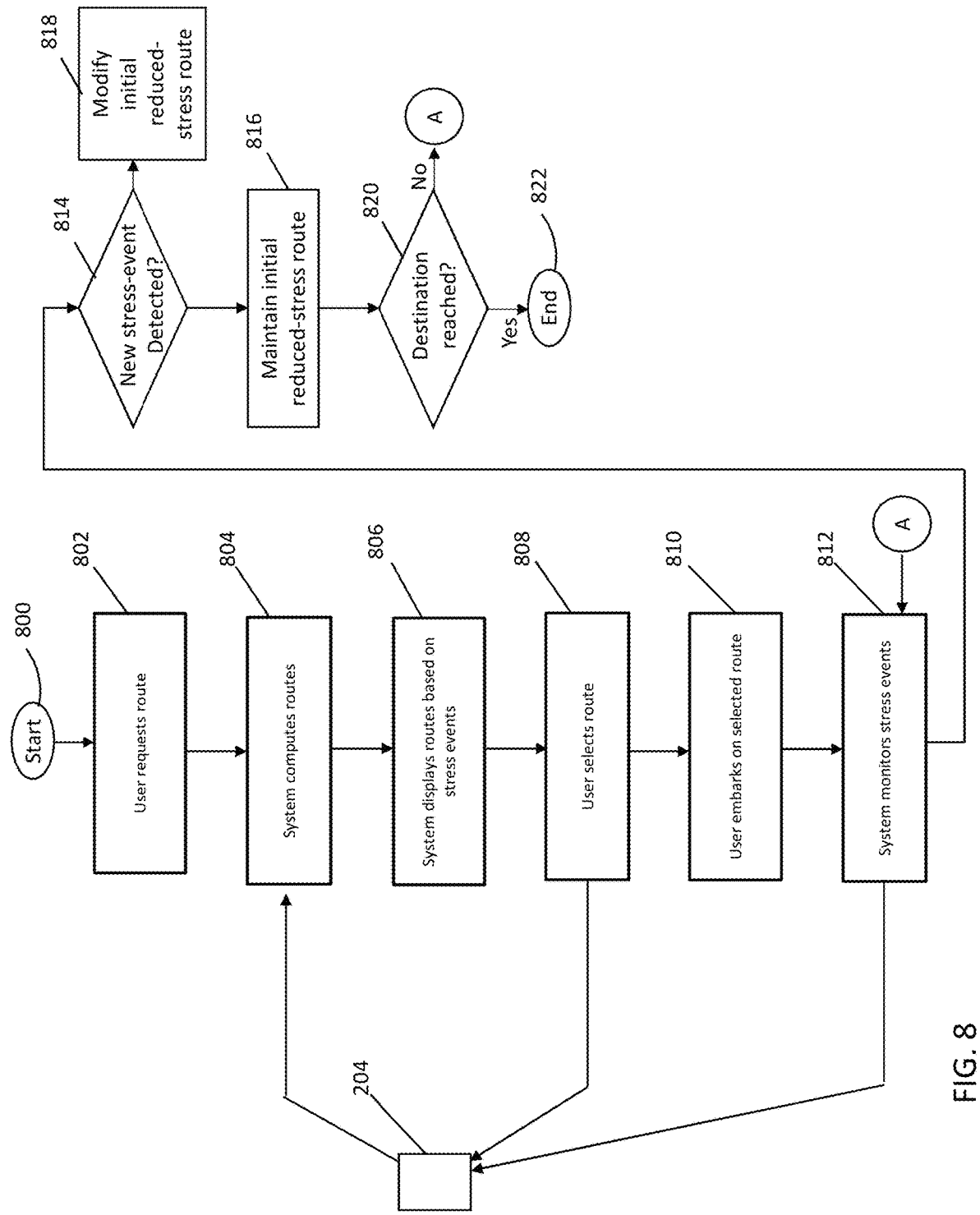
FIG. 8 depicts a flow diagram illustrating a method of determining one or more navigation routes based at least in part on a stress level of a user according to a non-limiting embodiment of the invention.

Turning to FIG. 8, a method of determining one or more navigation routes based at least in part on a stress level of a user is illustrated according to a non-limiting embodiment. The method begins at operation 800, and at operation 802 the communication device receives a request for navigation route. In one or more embodiments, the navigation route request can be input by a user that invokes a navigation app and inputs a desired destination (e.g., a destination address) and the user's starting point can be determined based on real-time GPS data provided by the communication device. At operation 804, the route server system 204 determines one or more navigation routes based on the starting point and the destination. Unlike conventional navigation route determining system, the route server system 204 described herein determines a user's present stress-level and/or predicts possible stress events the user may encounter while traveling from the starting point to the destination point. At operation 806, the communication device displays one or more navigation routes determined by the route server system 204. At least one of the navigation routes is a reduced-stress route, which takes into account the user's present stress level and/or a predicted possible stress event. For example, a first route may lead the user through an ongoing high-stress event such as icy road conditions, road construction, high traffic congestion, while the reduced-stress route identifies the ongoing high-stress event and leads the user to the destination while avoiding the high-stress event. At operation 808, the user selects a reduced-stress route and a graphical representation of the reduced stress route is displayed on the graphical map is displayed by the communication device. At operation 810, the user proceeds to the destination according to the reduced-stress route, and at operation 812 the route server system 204 actively monitors real-time user data, vehicle data and/or external data provided by sensors communicating with the communication device.

At operation 814, a determination is made as to whether a new stress-event is detected. For example, the route server system 204 can detect that a user's heart rate exceeds a BMP threshold while proceeding along the reduced-stress route and can further analyze vehicle data and/or external data to determine that the driver is experience an ongoing traffic congestion, a nearby aggressive driver, an unexpected inclement weather event, etc. When a new stress event is not detected, the initial or most recently generated reduced-stress route is maintained at operation 816. When, however, a new stress-event is detected at operation 814, the initial or most recently generated reduced-stress route is modified in real-time in order to re-route the user away from the newly detected stress event at operation 818. At operation 820, a determination is made as to whether the user has reached the destination. When the user has not yet reached the destination, the method returns to operation 812 and route server system 204 continues monitoring the real-time user data, vehicle data and/or external data. When, however, the reaches the destination, the method ends at operation 822.

As described herein, a real-time route determination system is provided, which determines one or more navigation routes that take into account a user's current stress-level and/or future or predicted stress events the user may encounter while traveling to the destination. The real-time route determination system described herein is configured to analyze a user's health and physiological data along with current GPS location data to detect increases in stress level, and then present a user with a route or modify the current route that avoids or reduces high-stress events.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

One or more of the methods described herein can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The present disclosure has been presented for purposes of illustration and description, but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the actions can be performed in a differing order or actions can be added, deleted or modified. Also, the term "coupled" describes having a signal path between two elements and does not imply a direct connection between the elements with no intervening elements/connections therebetween. All of these variations are considered a part of the present disclosure.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present disclosure can be a system, a method, and/or a computer program product. The computer program product can include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure can be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams can represent a module, segment, or portion of instructions, which comprises one or more executable instructions for implementing the specified logical function(s). In some alternative implementations, the functions noted in the block can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:
1. A real-time route determination system comprising:
at least one communication device configured to determine a stress-level;
a route server system in signal communication with the at least one communication device, the route server system configured to determine at least one navigation route in real-time based in part on the stress-level, the route server system configured to output a route signal indicative of the at least one navigation route,
wherein the route server system comprises:
a database configured to store a history of previous high-level stress events indexed to previous traffic congestion levels and historical external data, the historical external data including previous weather data, previous traffic congestion data, previous road construction data, previous lane closure data, and previous street closure data;
a real-time stress controller configured to obtain real-time vehicle data, real-time user data, and real-time external data, and to determine a real-time stress level of a user based on the real-time vehicle data, the real-time user data, and the real-time external data, the real-time external data including weather data, previous traffic congestion data, previous road construction data, previous lane closure data, and previous street closure data;
a stress predictor controller configured to predict a future stress event of the user;
a route determination controller in signal communication with the real-time stress controller and the stress predictor controller, the route determination controller configured to determine at least one navigation route based on one or both of the real-time stress level and the future stress level, wherein the stress predictor controller predicts the future stress event based on a comparison between the real-time vehicle data, the real-time user data, and the real-time external data and the previous traffic congestion levels and historical external data that are indexed to the previous high-level stress events stored in the database;

wherein the route server system determines the at least one navigation route in real-time based in part on the future stress event and the at least one communication device displays a graphical map including a graphical route displaying the at least one navigation route.

2. The real-time route determination system of claim 1, wherein the communication device is configured to receive one or both of vehicle data and user data, and to determine the stress-level based on one or both of the vehicle data and the user data, and wherein the at least one navigation route begins at a current real-time starting location of the at least one communication device and leads to a destination location so as to reduce the stress-level.

3. The real-time route determination system of claim 1, wherein the user data includes at least one user data type included in the group comprising heart rate, sweat, tension, body temperature, facial expressions, voice levels, and body movements, wherein the vehicle data includes at least one vehicle data type included in the group comprising real-time location of a given vehicle, real-time location data of vehicles near a given vehicle, real-time speed data of a given vehicle, braking data of a given vehicle, and real-time lane data of a given vehicle, and wherein the external data includes at least one external data type included in the group comprising weather data, traffic congestion data, road construction data, and lane closure data and street closure data.

4. A computer-implemented method to determine a navigation route in real-time, the computer-implemented method comprising:

receiving, via at least one communication device, one or both of real-time vehicle data and real-time user data;

determining a real-time stress-level based on one or both of the real-time vehicle data and the real-time user data;

storing, via a database, a history of previous high-level stress events indexed to previous traffic congestion levels and historical external data, the historical external data including previous weather data, previous traffic congestion data, previous road construction data, previous lane closure data, and previous street closure data;

determining, via a route server system in signal communication with the at least one communication device, at least one navigation route in real-time based in part on the stress-level;

obtaining, via a real-time stress controller, real-time vehicle data, real-time user data, and real-time external data, the real-time user data, and the real-time external data, the real-time external data including weather data, previous traffic congestion data, previous road construction data, previous lane closure data, and previous street closure data;

determining, via the real-time stress controller, a real-time stress level of a user based on the real-time vehicle data, the real-time user data, and the real-time external data, the real-time external data including weather data, previous traffic congestion data, previous road construction data, previous lane closure data, and previous street closure data;

predicting, via a stress predictor controller, a future stress event of the user based on a comparison between the real-time vehicle data, the real-time user data, and the real-time external data and the previous traffic congestion levels and historical external data that are indexed to the previous high-level stress events stored in the database;

determining, via a route determination controller, the route determination controller configured to determine at least one navigation route based on one or both of the real-time stress level and the future stress level;

outputting, via the route server system, a route signal indicative of the at least one navigation route; and displaying, via the at least one communication device, a graphical map including a graphical route displaying the at least one navigation route.

5. The computer implemented method of claim 4, wherein the at least one navigation route begins at a current real-time starting location of the at least one communication device and leads to a destination location so as to reduce the stress-level.

6. The computer implemented method of claim 4, wherein the user data includes at least one user data type included in the group comprising heart rate, sweat, tension, body temperature, facial expressions, voice levels, and body movements, wherein the vehicle data includes at least one vehicle data type included in the group comprising real-time location of a given vehicle, real-time location data of vehicles near a given vehicle, real-time speed data of a given vehicle, braking data of a given vehicle, and real-time lane data of a given vehicle, and wherein the external data includes at least one external data type included in the group comprising weather data, traffic congestion data, road construction data, and lane closure data and street closure data.

7. A computer program product comprising a non-transitory storage medium readable by a processing circuit and storing instructions for execution by the processing circuit for performing a method to determine a navigation route in real-time, the method comprising:

receiving, via at least one communication device, one or both of real-time vehicle data and real-time user data;

determining a real-time stress-level based on one or both of the real-time vehicle data and the real-time user data;

storing, via a database, a history of previous high-level stress events indexed to previous traffic congestion levels and historical external data, the historical external data including previous weather data, previous traffic congestion data, previous road construction data, previous lane closure data, and previous street closure data;

determining, via a route server system in signal communication with the at least one communication device, at least one navigation route in real-time based in part on the stress-level;

determining, via a real-time stress controller, the real-time stress level of a user based at least in part on the user data;

obtaining, via a real-time stress controller, real-time vehicle data, real-time user data, and real-time external data, the real-time user data, and the real-time external data, the real-time external data including weather data, previous traffic congestion data, previous road construction data, previous lane closure data, and previous street closure data;

determining, via the real-time stress controller, a real-time stress level of a user based on the real-time vehicle data, the real-time user data, and the real-time external data, the real-time external data including weather data, previous traffic congestion data, previous road construction data, previous lane closure data, and previous street closure data predicting, via a stress predictor controller, a future stress event of the user based on a comparison between the real-time vehicle data, the real-time user data, and the real-time external data and the previous traffic congestion levels and historical external data that are indexed to the previous high-level stress events stored in the database;

determining, via a route determination controller, the route determination controller configured to determine at least one navigation route based on one or both of the real-time stress level and the future stress level;

outputting, via the route server system, a route signal indicative of the at least one navigation route; and displaying, via the at least one communication device, a graphical map including a graphical route displaying the at least one navigation route.

8. The computer implemented method of claim 7, wherein the at least one navigation route begins at a current real-time starting location of the at least one communication device and leads to a destination location so as to reduce the stress-level.

\* \* \* \* \*